United States Patent
Fukuwara et al.

(10) Patent No.: US 8,576,987 B2
(45) Date of Patent: Nov. 5, 2013

(54) X-RAY DIAGNOSTIC APPARATUS AND X-RAY DIAGNOSTIC METHOD INCLUDING SWITCHING AN X-RAY GENERATOR FROM AN ABNORMAL HIGH VOLTAGE GENERATOR TO A NORMAL HIGH VOLTAGE GENERATOR

(75) Inventors: Manabu Fukuwara, Otawara (JP); Mitsuru Sakata, Yaita (JP); Katsuie Ikawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 234 days.

(21) Appl. No.: 12/892,469

(22) Filed: Sep. 28, 2010

(65) Prior Publication Data

US 2011/0129067 A1 Jun. 2, 2011

(30) Foreign Application Priority Data

Nov. 30, 2009 (JP) ................... 2009-271666

(51) Int. Cl.
- *H05G 1/10* (2006.01)
- *H05G 1/26* (2006.01)
- *H05G 1/32* (2006.01)
- *H05G 1/58* (2006.01)

(52) U.S. Cl.
USPC ............ 378/117; 378/101; 378/115; 378/116

(58) Field of Classification Search
USPC ............ 378/92, 101–107, 114, 115, 117, 118
See application file for complete search history.

(56) References Cited

U.S. PATENT DOCUMENTS

| | | | | |
|---|---|---|---|---|
| 3,333,104 A | * | 7/1967 | Bougle | 378/92 |
| 3,450,880 A | * | 6/1969 | Mook | 378/92 |
| 4,317,039 A | * | 2/1982 | Romandi | 378/105 |
| 4,734,924 A | * | 3/1988 | Yahata et al. | 378/118 |
| 5,923,549 A | | 7/1999 | Kobayashi et al. | |
| 5,923,721 A | * | 7/1999 | Duschka | 378/92 |
| 6,198,790 B1 | * | 3/2001 | Pflaum | 378/9 |

(Continued)

FOREIGN PATENT DOCUMENTS

CN    1736335 A    2/2006

OTHER PUBLICATIONS

Chinese Office Action issued Feb. 29, 2012, in Patent Application No. 201010514682.X.

(Continued)

*Primary Examiner* — Allen C. Ho
(74) *Attorney, Agent, or Firm* — Oblon, Spivak, McClelland, Maier & Neustadt, L.L.P.

(57) ABSTRACT

According to one embodiment, an X-ray diagnostic apparatus includes X-ray generators, X-ray detectors, high voltage generators, a switching device, an abnormality detection unit and a control unit. The high voltage generators are configured to apply voltages to the X-ray generators. The switching device is configured to switch outputs from the high voltage generators to the X-ray generators. The abnormality detection unit is configured to detect an abnormality in the high voltage generators. The control unit is configured to control the switching device to switch from an output from a high voltage generator of which abnormality has been detected by the abnormality detection unit toward a corresponding X-ray generator to an output from another high voltage generator toward the corresponding X-ray generator.

6 Claims, 10 Drawing Sheets

(56) References Cited

U.S. PATENT DOCUMENTS

| | | | |
|---|---|---|---|
| 6,426,997 B1 * | 7/2002 | Fuchs et al. | 378/118 |
| 6,435,713 B1 * | 8/2002 | Iizuka | 378/195 |
| 6,990,175 B2 * | 1/2006 | Nakashima et al. | 378/65 |
| 7,050,539 B2 * | 5/2006 | Loef et al. | 378/105 |
| 7,085,343 B2 * | 8/2006 | Shinno et al. | 378/9 |
| 7,233,645 B2 * | 6/2007 | Feda | 378/102 |
| 7,852,986 B2 * | 12/2010 | Loef et al. | 378/111 |
| 2003/0076920 A1 | 4/2003 | Shinno et al. | |

OTHER PUBLICATIONS

Office Action issued Jul. 16, 2013 in Chinese Patent Application No. 201010514682.X.

* cited by examiner

| DETECTED ABNORMALITY | INVERTER DRIVE CIRCUIT | | | | SWITCHING DEVICE | | | | OPERATION PANEL DISPLAY | | |
|---|---|---|---|---|---|---|---|---|---|---|---|
| | 71e | 72e | 73e | 74e | 12 | 13 | 14 | 15 | R1 OP | R2 OP | BIPLANE |
| NORMAL | OPR | OPR | OPR | OPR | 12a 12c ON | 13a 13c ON | 14a 14c ON | 15a 15c ON | FULL | FULL | POSSIBLE |
| | HALT | OPR | OPR | OPR | OFF | OFF | 14b 14d ON | 15a 15c ON | NOT FULL | NOT FULL | POSSIBLE |
| POWER ABNORMALITY | HALT | HALT | OPR | OPR | OFF | OFF | 14a 14c ON | 15a 15c ON | 0 | FULL | IMPOSSIBLE |
| | HALT | HALT | OPR | OPR | OFF | OFF | 14b 14d ON | 15b 15d ON | FULL | 0 | IMPOSSIBLE |
| | OPR | HALT | OPR | OPR | 12a 12c ON | OFF | 14a 14c ON | 15a 15c ON | NOT FULL | FULL | POSSIBLE |
| INVERTER ABNORMALITY | OPR | HALT | OPR | OPR | 12a 12c ON | OFF | 14b 14d ON | 15a 15c ON | FULL | NOT FULL | POSSIBLE |

X-RAY DIAGNOSTIC APPARATUS AND X-RAY DIAGNOSTIC METHOD INCLUDING SWITCHING AN X-RAY GENERATOR FROM AN ABNORMAL HIGH VOLTAGE GENERATOR TO A NORMAL HIGH VOLTAGE GENERATOR

CROSS REFERENCES TO RELATED APPLICATIONS

This application is based upon and claims the benefit of priority from Japanese Patent Application No. 2009-271666, filed Nov. 30, 2009; the entire contents of which are incorporated herein by reference.

BACKGROUND

1. Field

Embodiments described herein relate generally to an X-ray diagnostic apparatus and an X-ray diagnostic method.

2. Description of the Related Art

X-ray diagnostic apparatuses include a biplane type of X-ray diagnostic apparatus which can irradiate X-rays to an object from different directions to obtain three dimensional information in a diagnosis part. The biplane type of X-ray diagnostic apparatus has two sets of X-ray tubes and detectors. Each X-ray tube works as an X-ray source while each detector detects X-ray. The biplane type of X-ray diagnostic apparatus also has high voltage generators dedicated to the respective X-ray tubes.

In recent years, an inverter type of high voltage generator having a high power semiconductor device becomes popular as a high voltage generator for a medical X-ray system. This inverter type of high voltage generator has a characteristic that it is possible to save a space by using a high frequency to make a size and weight of the high voltage generator small and to form a nearly constant tube voltage waveform with either a single-phase power or a three-phase one to obtain a high efficiency.

For example, an X-ray diagnostic apparatus for a diagnosis of circulatory organ is often used for a treatment as well as an examination. For that reason, when an output of X-ray stops while a doctor manipulates a catheter in an operation for example, it becomes difficult to manipulate the catheter, which makes a risk against an object high.

Accordingly, the stable operation of an X-ray diagnostic apparatus is very important and a high reliability is strongly required for an X-ray diagnostic apparatus. For that reason, an X-ray diagnostic apparatus having high voltage generators is offered (refer to the patent document 1: Japanese Publication of Patent Application No. 10-27697). This apparatus can continue to output an X-ray even if an abnormality occurs in one of the high voltage generators each including an inverter.

However, the invention disclosed in the above patent document 1 does not consider following points.

That is, the medical X-ray system shown in the above patent document 1 includes only one set of X-ray tube serving as an X-ray source and detector detecting an X-ray. Therefore, two high voltage generators are provided for one X-ray tube. Application of plural high voltage generators with a biplane type of X-ray diagnostic apparatus, which has two sets of X-ray tubes each serving as an X-ray source and detectors each detecting an X-ray, is not described in the patent document 1.

The biplane type of X-ray diagnostic apparatus has a characteristic that three dimensional information of a diagnosis part can be acquired by exposures of X-rays from different directions as described above. Therefore, it is preferable to adopt a configuration that the first high voltage generator for the first plane (imaging system) can power the second plane (imaging system), in order to exert the characteristic with keeping a stable operation of the apparatus. This configuration makes it possible to continue to use the X-ray diagnostic apparatus as the biplane type safely even if an abnormality occurs in one high voltage generator for one plane (imaging system).

On the other hand, one plane of a biplane type of X-ray diagnostic apparatus may be used preferentially depending on a diagnosis object for example. When the plane which cannot be used due to an abnormality is one which should be used preferentially, it is preferable to operate the plane which should be used preferentially even if the other plane stops or an output from the other plane is limited. Alternatively, providing plural high voltage generators with each plane so as to address an abnormality may make a circuitry of X-ray diagnostic apparatus complex and the apparatus expensive.

BRIEF DESCRIPTION OF THE DRAWINGS

In the accompanying drawings:

FIG. 10 is a table showing an example of method for controlling the circuit shown in FIG. 9 in case where an abnormality occurred in a part of the circuit

DETAILED DESCRIPTION

In general, according to one embodiment, an X-ray diagnostic apparatus includes X-ray generators, X-ray detectors, high voltage generators, a switching device, an abnormality detection unit and a control unit The X-ray detectors correspond to the X-ray generators. The high voltage generators are configured to apply voltages to the X-ray generators. The switching device is configured to switch outputs from the high voltage generators to the X-ray generators. The abnormality detection unit is configured to detect an abnormality in the high voltage generators. The control unit is configured to control the switching device to switch from an output from a high voltage generator of which abnormality has been detected by the abnormality detection unit toward a corresponding X-ray generator to an output from another high voltage generator toward the corresponding X-ray generator.

Further, according to another embodiment, an X-ray diagnostic method includes detecting an abnormality in high voltage generators for applying voltages to X-ray generators; switching an output from a high voltage generator of which abnormality has been detected toward a corresponding X-ray generator to an output from another high voltage generator toward the corresponding X-ray generator, detecting projection data of an object by exposing an X-ray to the object using at least the corresponding X-ray generator, and generating image data based on the detected projection data Hereinafter, embodiments of the present invention will be described in detail with referring to drawings.

(First Embodiment)

Figure 1:
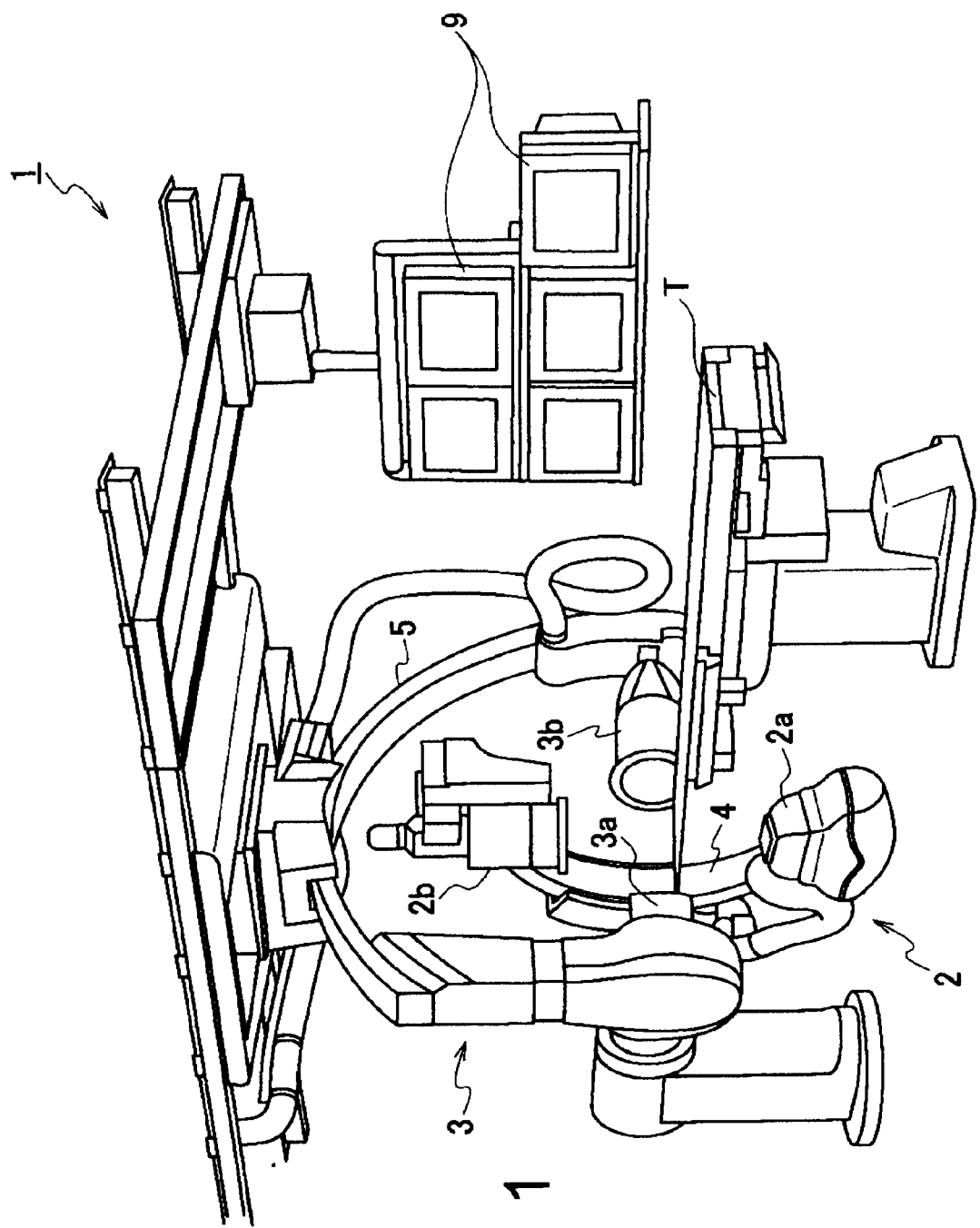
FIG. 1 is an oblique perspective view showing a whole X-ray diagnostic apparatus according to an embodiment of the present invention.

FIG. 1 is an oblique perspective view showing a whole X-ray diagnostic apparatus 1 according to an embodiment of the present invention. The X-ray diagnostic apparatus 1 includes a first imaging system 2 and a second imaging system 3. The first imaging system 2 has a first X-ray generator 2a and a first X-ray detector 2b. The first X-ray generator 2a and the first X-ray detector 2b are arranged so that an object, which is not shown and set on a top plate T of a bed, intervenes between the first X-ray generator 2a and the first X-ray detector 2b. The second imaging system 3 has a second X-ray generator 3a and a second X-ray detector 3b. The second X-ray generator 3a and the second X-ray detector 3b are also arranged so that the object intervenes between the second X-ray generator 3a and the second X-ray detector 3b. That is, X-ray diagnostic apparatus 1 according to the embodiment of the present invention is a so-called biplane type of X-ray diagnostic apparatus having plural imaging systems.

The first X-ray generator 2a and the first X-ray detector 2b included in the first imaging system 2 are arranged at both end parts of a first supporting structure 4 respectively. Meanwhile, the second X-ray generator 3a and the second X-ray detector 3b included in the second imaging system 3 are arranged at both end parts of a second supporting structure 5 respectively. The first supporting structure 4 is independent from the second supporting structure 5 and they can be driven separately.

Figure 2:
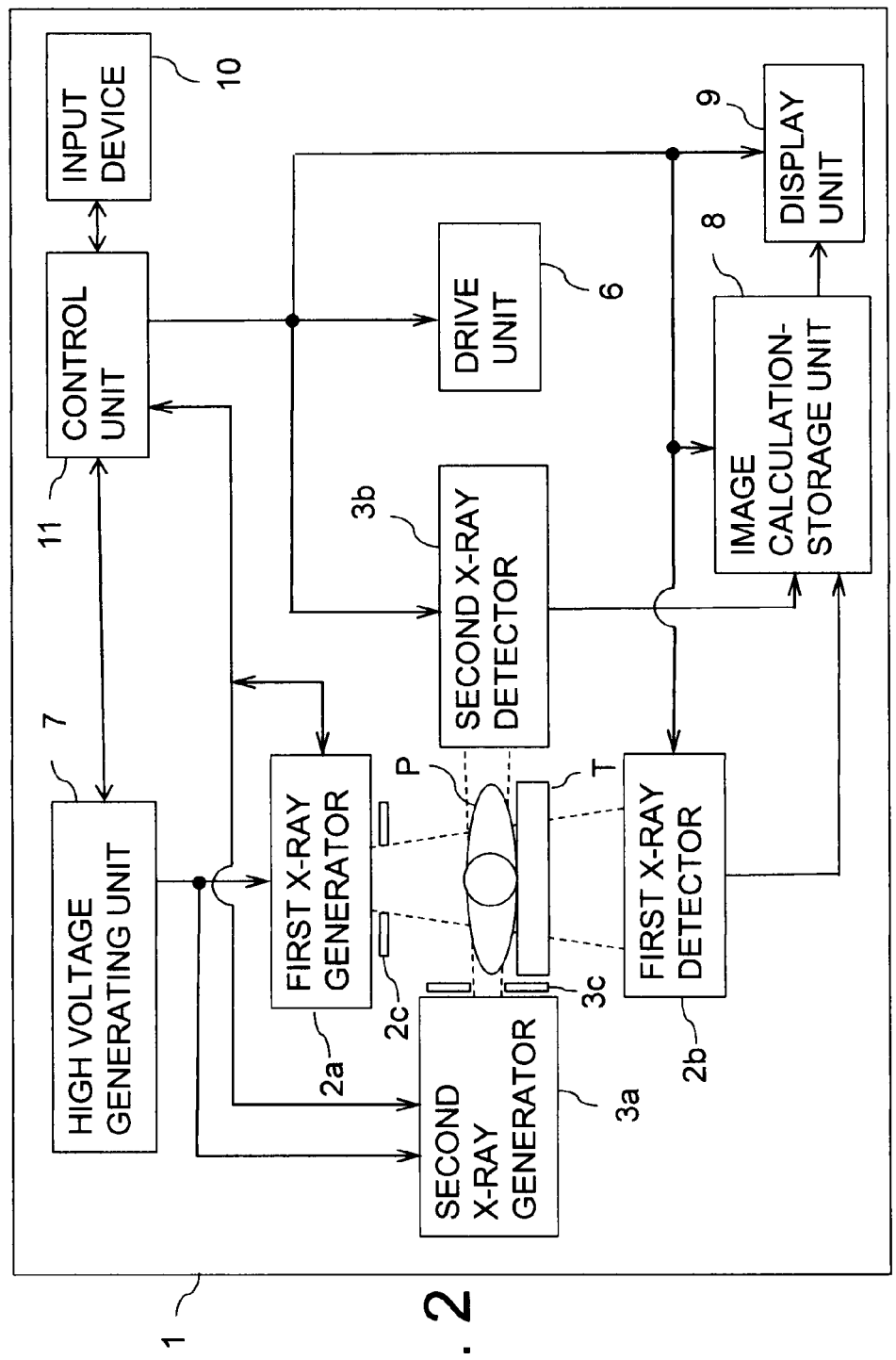
FIG. 2 is a block diagram showing a whole configuration of the X-ray diagnostic apparatus according to an embodiment of the present invention.

The X-ray diagnostic apparatus 1 also includes a display unit 9 for displaying image data FIG. 2 is a block diagram showing a whole configuration of the X-ray diagnostic apparatus 1 according to an embodiment of the present invention. The X-ray diagnostic apparatus 1 is configured to allow imaging of the object P set on the top plate T from two directions as shown in FIG. 2. Imaging from one direction is performed by the first imaging system 2 and imaging from the other direction is performed by the second imaging system 3. The imaging systems have the X-ray generators 2a and 3a and the X-ray detectors 2b and 3b respectively as mentioned above.

Note that, operations of the respective driving elements of the X-ray diagnostic apparatus 1 including the first supporting structure 4 and the second supporting structure 5 shown in FIG. 1, which are omitted in FIG. 2, are controlled by a drive unit 6.

Each of the first X-ray generators 2a and the second X-ray generators 3a has an X-ray tube R not shown in FIG. 2 and an aperture device 2c or 3c. The X-ray tube R exposes an X-ray to an object P. The respective aperture devices 2c and 3c form X-ray cone beams using X-rays exposed from the X-ray tubes R respectively. The X-ray tube R is a vacuum tube which generates an X-ray by accelerating electrons released from a cathode (filament) under a high voltage to collide with a tungsten anode. Each of the aperture devices 2c and 3c is arranged between the object P and the corresponding X-ray tubes R. The aperture devices 2c and 3c have functions to narrow down the X-ray beams exposed from the X-ray tubes R into specific sizes of exposure ranges on the X-ray detectors 2b and 3b respectively It is a high voltage generating unit 7 that applies a high voltage with the first X-ray generators 2a and the second X-ray generators 3a. A detail configuration of the high voltage generating unit 7 according to the embodiment of the present invention will be described later.

Each of the first X-ray detector 2b and the second X-ray detector 3b detects projection data of the object P to which an X-ray is exposed. As an X-ray detector, an X-ray I.I. (image intensifier) and a so-called X-ray plane detector (two dimensional arrayed X-ray detector) on which X-ray detection elements are arrayed two dimensionally can be adopted.

The information detected in the first X-ray detector 2b or the second X-ray detector 3b is sent to an image calculation-storage unit 8. The image calculation-storage unit 8 generates volume data by reconstruction processing based on the received information. Further, three dimensional image data and two dimensional image data such as MPR (Multi-Planar Reconstruction) image data are generated based on the volume data The generated image data is transmitted to and displayed on the display unit 9.

The operations of the first imaging system 2, the second imaging system 3, the drive unit 6, the high voltage generating unit 7, the image calculation-storage unit 8 and the display unit 9 mentioned above are controlled according to control signals from a control unit 11, based on instructions inputted from an input device 10 or procedures stored in a storage unit included in the X-ray diagnostic apparatus 1.

Figure 3:
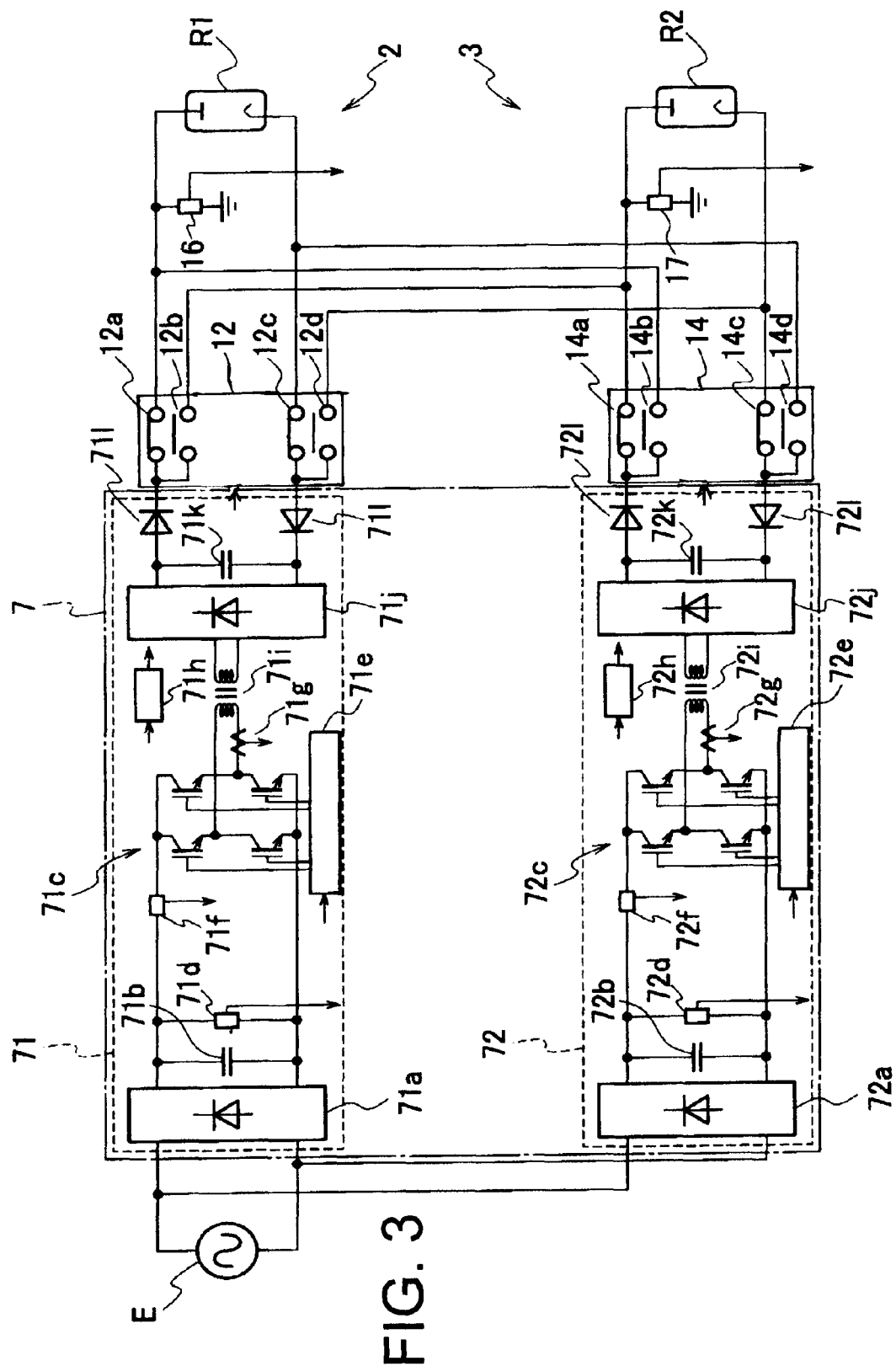
FIG. 3 is a circuit schematic showing a circuit configuration of the high voltage generator according to the first embodiment of the present invention.

FIG. 3 is a circuit schematic mainly showing a circuit configuration of the high voltage generator 7 according to the first embodiment of the present invention. As shown in FIG. 3, this circuit schematic shows a connection configuration from a commercial power E to the X-ray generators (the X-ray tubes R) of the first imaging system 2 and the second imaging system 3 through the high voltage generating unit 7 and switching devices 12 and 14. In the first embodiment, one high voltage generator is provided with each of the first imaging system 2 and the second imaging system 3. The circuit configuration from the commercial power E to the first X-ray generators 2a (a first X-ray tube R1) is same as that from the commercial power E to the second X-ray generators 3a (a second X-ray tube R2). Therefore, explanations in circuit configurations of the first imaging system 2 and the second imaging system 3 are made collectively in FIG. 3.

Note that, a high voltage generator which is connected with the commercial power E and applies a direct current high voltage with the first X-ray tube R1 described later is represented as a first high voltage generator 71 while a high voltage generator which is connected with the commercial power E and applies a direct current high voltage with the second X-ray tube R2 described later is represented as a second high voltage generator 72 for convenience here.

As shown in FIG. 3, powers are supplied to the first imaging system 2 and the second the imaging system 3 from the same commercial power E. Alternating currents supplied from the commercial power E become direct currents by rectifications in full wave rectifying circuits 71a and 72a and smoothing in condensers 71b and 72b respectively. The direct currents are supplied to inverter circuits 71c and 72c having semiconductor devices for a high power (high-speed and high-capacity switching elements) respectively. FIG. 3 shows IGBTs (Insulated Gate Bipolar Transistors) for example. The voltage values supplied from the commercial power E to the inverter circuits 71c and 72c are detected by voltage detection devices 71d and 72d connected with the condensers 71b and 72b in parallel at upstream of the inverter circuits 71c and 72c respectively.

The inverter circuits 71c and 72c are driven by inverter drive circuits 71e and 72e respectively. Further, fuses 71f and 72f with fuse shutoff detection devices are inserted in one ends as input sides of the inverter circuits 71c and 72c while current detection devices 71g and 72g are inserted in the other ends as output sides of the inverter circuits 71c and 72c respectively. In addition, temperature detection devices 71h and 72h are connected with the inverter circuits 71c and 72c respectively. The temperature detection devices 71h and 72h detect temperatures of the inverter circuits 71c and 72c respectively.

The direct currents are changed into the alternating currents having high frequencies by the inverter circuits 71c and 72c, and subsequently, the alternating currents having the high frequencies are pressurized into alternating currents having high voltages by high voltage transformers 71i and 72i respectively. Then, high voltage direct currents smoothed by high voltage rectifier 71j and 72j and condensers 71k and 72k are applied to the first X-ray tube R1 and the second X-ray tube R2 through the switching devices 12 and 14 respectively. The high voltage rectifier 71j and 72j consist of high pressure tight silicon rectifiers and the like.

Further, diodes 71l and 72l are connected between the condensers 71k and 72k and the switching devices 12 and 14 respectively. Voltage divider resistances not shown are connected between the switching devices 12 and 14 and the first X-ray tube R1 and the second X-ray tube R2 respectively. The voltages after voltage divide by the voltage divider resistances are sent to the control unit 11 as detected tube voltage values (detected values corresponding to voltages applied to the X-ray tubes R) through tube voltage detection devices 16 and 17 respectively.

Each of the voltage detection devices 71d and 72d, the fuse shutoff detection devices of the fuses 71f and 72f, the current detection devices 71g and 72g and the temperature detection devices 71h and 72h functions as an abnormality detection unit. The pieces of information detected by the respective devices are sent to the control unit 11. In FIG. 3, the pieces of information sent to the control unit 11 are indicated with arrows of solid lines outputted from the respective abnormality detection units. The control unit 11 controls the inverter drive circuits 71e and 72e and the switching devices 12 and 14 based on these pieces of information. In FIG. 3, control signals from the control unit 11 are indicated with arrows of solid lines toward the inverter drive circuits 71e and 72e and the switching devices 12 and 14.

The switching device 12 has four switches 12a, 12b, 12c and 12d. Similarly, the switching device 14 has four switches 14a, 14b, 14c and 14d.

In the first embodiment, the high voltage generators 71 and 72 corresponding to the first imaging system 2 and the second imaging system 3 respectively are set as mentioned above. Generally, the high voltage from the first high voltage generator 71 is supplied to the first X-ray tube R1 in general because the switches 12a and 12c are closed as shown in FIG. 3. Similarly, the high voltage from the second high voltage generator 72 is supplied to the second X-ray tube R2 because the switches 14a and 14c are closed.

However, the systems each constituted by the high voltage generator and the X-ray tube are not perfectly independent from each other. That is, each X-ray tube is connected with the other high voltage generator between the switching device 12 and the first X-ray tube R1 or between the switching device 14 and the second X-ray tube R2. More specifically, the switch 14b is connected between the switch 12a and the first X-ray tube R1, the switch 14d is connected between the switch 12c and the first X-ray tube R1, the switch 12b is connected between the switch 14a and the second X-ray tube R2, and the switch 12d is connected between the switch 14c and the second X-ray tube R2.

In other words, closing the two switches 12a and 12c of the switching device 12 establishes the connection between the first high voltage generator 71 and the first X-ray tube R1 while closing the two switches 12b and 12d establishes the connection between the first high voltage generator 71 and the second X-ray tube R2. On the other hand, closing the two switches 14a and 14c of the switching device 14 establishes the connection between the second high voltage generator 72 and the second X-ray tube R2 while closing the two switches 14b and 14d establishes the connection between the second high voltage generator 72 and the first X-ray tube R1.

Under such connections, it is possible to apply a high voltage from the first high voltage generator 71 to the second X-ray tube R2 or a high voltage from the second high voltage generator 72 to the first X-ray tube R1 by switching the switching devices 12 and 14.

Figure 4:
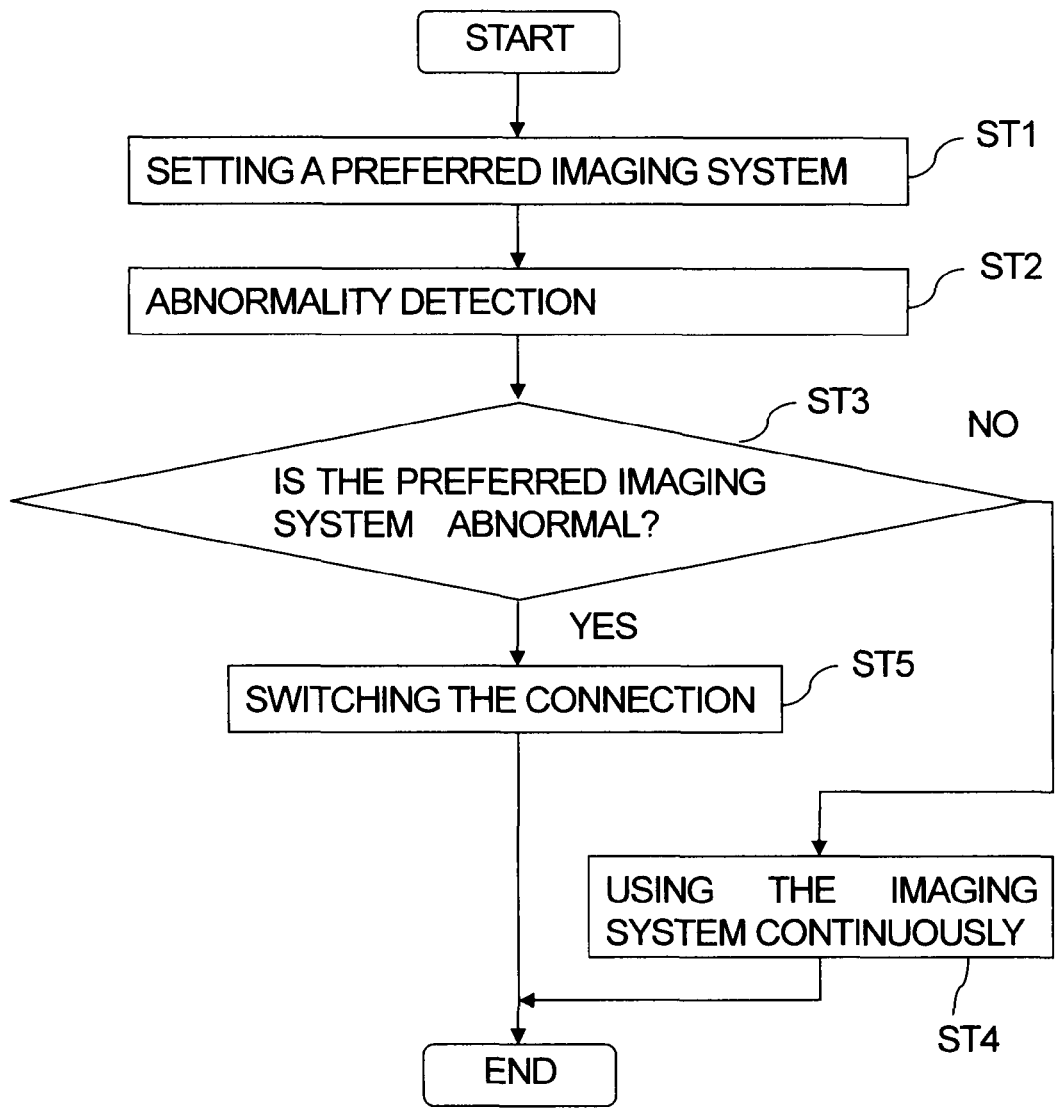
FIG. 4 is a flowchart showing a flow of a rough control in case where an abnormality occurred in the X-ray diagnostic apparatus according to the first embodiment of the present invention.

Next, a control in the X-ray diagnostic apparatus 1 in case where the abnormality detection unit detects an abnormality in the high voltage generating unit 7 will be described. FIG. 4 is a flowchart showing a flow of a rough control in case where an abnormality occurred in the X-ray diagnostic apparatus 1 according to the first embodiment of the present invention.

The X-ray diagnostic apparatus 1 according to the first embodiment of the present invention is a so-called biplane type of X-ray diagnostic apparatus as mentioned above. Therefore, two imaging systems are provided with the X-ray diagnostic apparatus 1. Which imaging system is mainly used in the biplane type use and whether only one imaging system is used as a single plane type use are selectable by an operator. Actually, an appropriate selection is made depending on a diagnosis object, an examination detail such as examination respects and examination parts, and the like.

Accordingly, a preferentially used imaging system is set in advance (ST1). For example, the setting is automatically made by selecting an examination content. Of course, inputting various conditions individually with operating the input device 10 by the operator also can set a preferentially used imaging system. After the setting, the operator performs examination and diagnosis of an object P with the X-ray diagnostic apparatus 1.

If a certain abnormality occurs in the X-ray diagnostic apparatus 1 in use, the abnormality detection unit detects the abnormality (ST2). For example, a temperature detection device 71h and 72h detects that a temperature of a switching element constituting an inverter circuit 71c and 72c has risen beyond a specific temperature.

The control unit 11 which received a signal from the abnormality detection unit determines whether the imaging system of which abnormality has been detected is the imaging system set as a preferentially used imaging system or not (ST3). The control unit 11 recognizes the imaging system of which abnormality has been detected to determine which high voltage generator is to apply a high voltage to which X-ray tube R based on the recognized state.

When the imaging system of which abnormality has been detected by the abnormality detection unit is not the preferentially used imaging system (NO in ST3), the preferentially used imaging system is used continuously as it is (ST4).

A detail explanation will be given with the relationship between the high voltage generating unit 7 and X-ray tubes R of the first embodiment for example. As mentioned above, the first high voltage generator 71 receives a power from the commercial power E to apply a high voltage to the first X-ray tube R1. On the other hand, the second high voltage generator 72 receives a power from the commercial power E to apply a high voltage to the second X-ray tube R2. Then, the first imaging system 2 including the first X-ray tube R1 is set to be the preferentially used imaging system for example (refer to ST1).

In this case, when an abnormality detection unit, which is one of the voltage detection device 72d, the fuse shutoff detection device of the fuse 72f, the current detection device 72g and the temperature detection device 72h, detects an abnormality in the second high voltage generator 72 corresponding to the second imaging system (refer to ST2), the control unit 11 recognizes the abnormality. Further, the control unit 11 recognizes that the high voltage generator of which abnormality has been detected is the high voltage generator 72 supplying a high voltage to the second imaging system 3 which is not set to be the preferentially used one (ST3). That is, the control unit 11 controls the switching devices 12 and 14 so that the first imaging system 2 continues to be used as it is because no abnormality has been detected in the preferentially used imaging system which is the first imaging system 2.

On the other hand, the second high voltage generator 72 of which abnormality has been detected cannot apply a high voltage to the second X-ray tube R2 stably. For that reason, the switches 14a and 14c are opened so as to shut off the second high voltage generator 72 of which abnormality has been detected from the second X-ray tube R2.

When the imaging system of which abnormality has been detected by the abnormality detection unit is the preferentially used imaging system (YES in ST3), the switching devices 12 and 14 are switched so that the preferentially used imaging system receives a high voltage from the normal high voltage generator of which abnormality has not been detected, in order to use the preferentially used imaging system (ST5).

Figure 5:
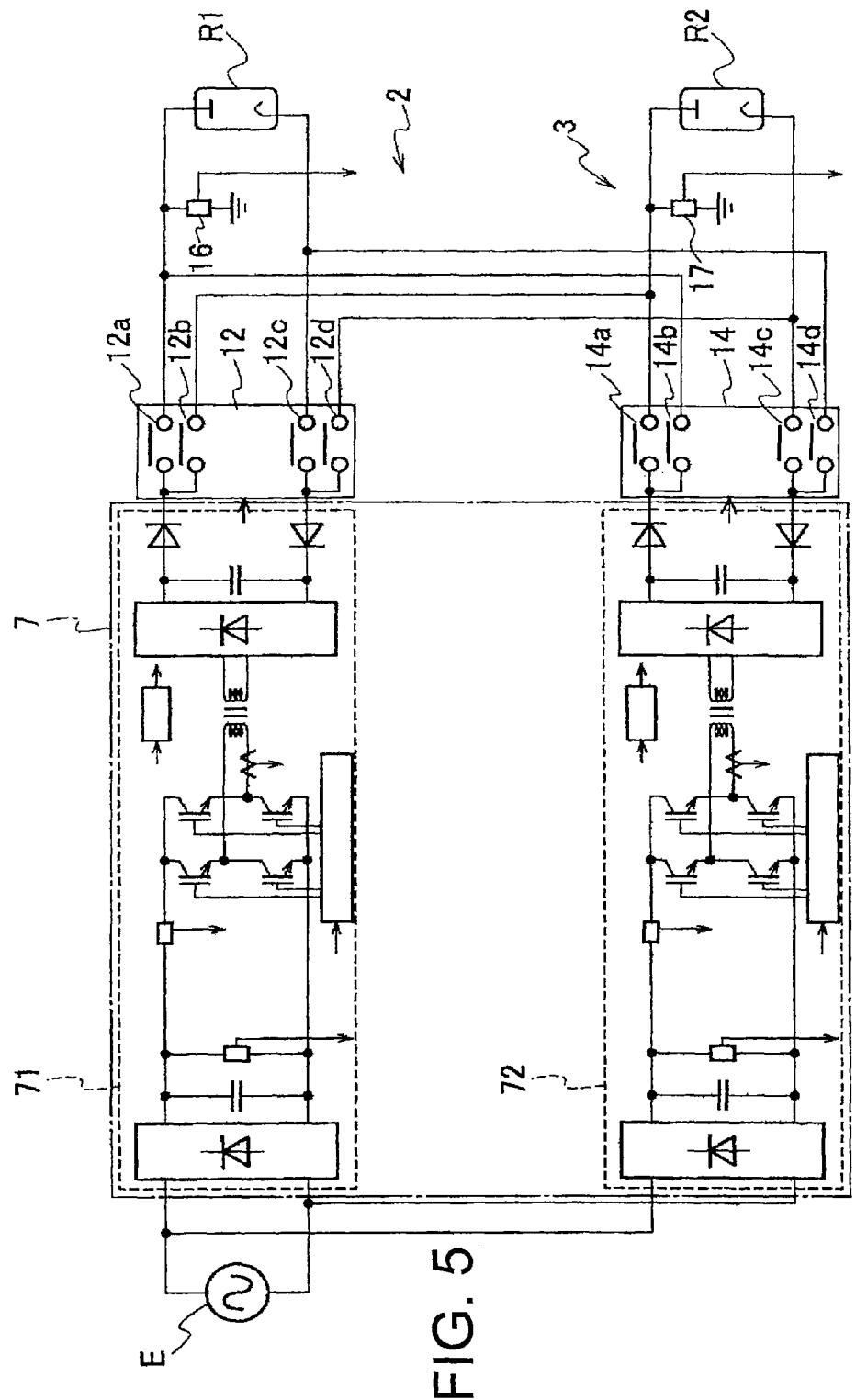
FIG. 5 is a circuit schematic showing a configuration of the circuit shown in FIG. 3 in case where an abnormality occurred in a part of the circuit

This flow will be described with referring to FIG. 5. FIG. 5 is a circuit schematic showing a configuration of the circuit shown in FIG. 3 in case where an abnormality occurred in a part of the circuit. FIG. 5 shows a circuit configuration in case where an abnormality was detected in the first high voltage generator 71 though the first imaging system 2 had been set as the preferentially used imaging system. On the other hand, the second high voltage generator 72 works normally though the second imaging system 3 is not set as the preferentially used imaging system.

In such a case, the control unit 11 recognizes that an abnormality has been detected in the first high voltage generator 71 corresponding to the first imaging system 2 which has been set as the preferentially used imaging system, based on information sent from the abnormality detection unit (YES in ST3). After that, the switches 12a and 12c, which have been closed, are opened to shut off the first high voltage generator 71 of which abnormality has been detected from the first X-ray tube R1. The switches 12b and 12d are opened originally. Therefore, opening the switches 12a and 12c shuts off the first high voltage generator 71 from the first X-ray tube R1. Subsequently, the switches 14a and 14c, connecting the second high voltage generator 72 with the second X-ray tube R2, are opened while switches 14b and 14d are closed (refer to ST5).

That is, opening and closing of the switching devices 12 and 14 as mentioned above connects the first X-ray tube R1 with the switches 14b and 14d. Therefore, a high voltage from the normal second high voltage generator 72 can be applied to the first imaging system 2 (the first X-ray tube R1) set as the preferentially used imaging system.

Under such a control, a high voltage is applied to the preferentially used imaging system steadily. Therefore, even though an abnormality occurs in a high voltage generator corresponding to one plane necessary for diagnosis, the one plane can be used continuously by an output from a high voltage generator corresponding to the other plane with adopting an inexpensive configuration. Consequently, a restriction in use of an apparatus due to an abnormality can be narrowed to increase safety of an object and a biplane type of X-ray diagnostic apparatus which keeps convenience to an operator can be obtained.

(Second Embodiment)

Next, the second embodiment of the present invention will be described. Note that, the explanation for the same elements of the second embodiment as those explained in the above-mentioned first embodiment is omitted for avoiding duplication.

The second embodiment is different from the first embodiment in the point that plural (two) high voltage generators are provided to apply high voltages to one imaging system. On the other hand, the second embodiment is similar to the first embodiment in the point that a single high voltage generator is provided to apply a high voltage to the other imaging system.

Figure 6:
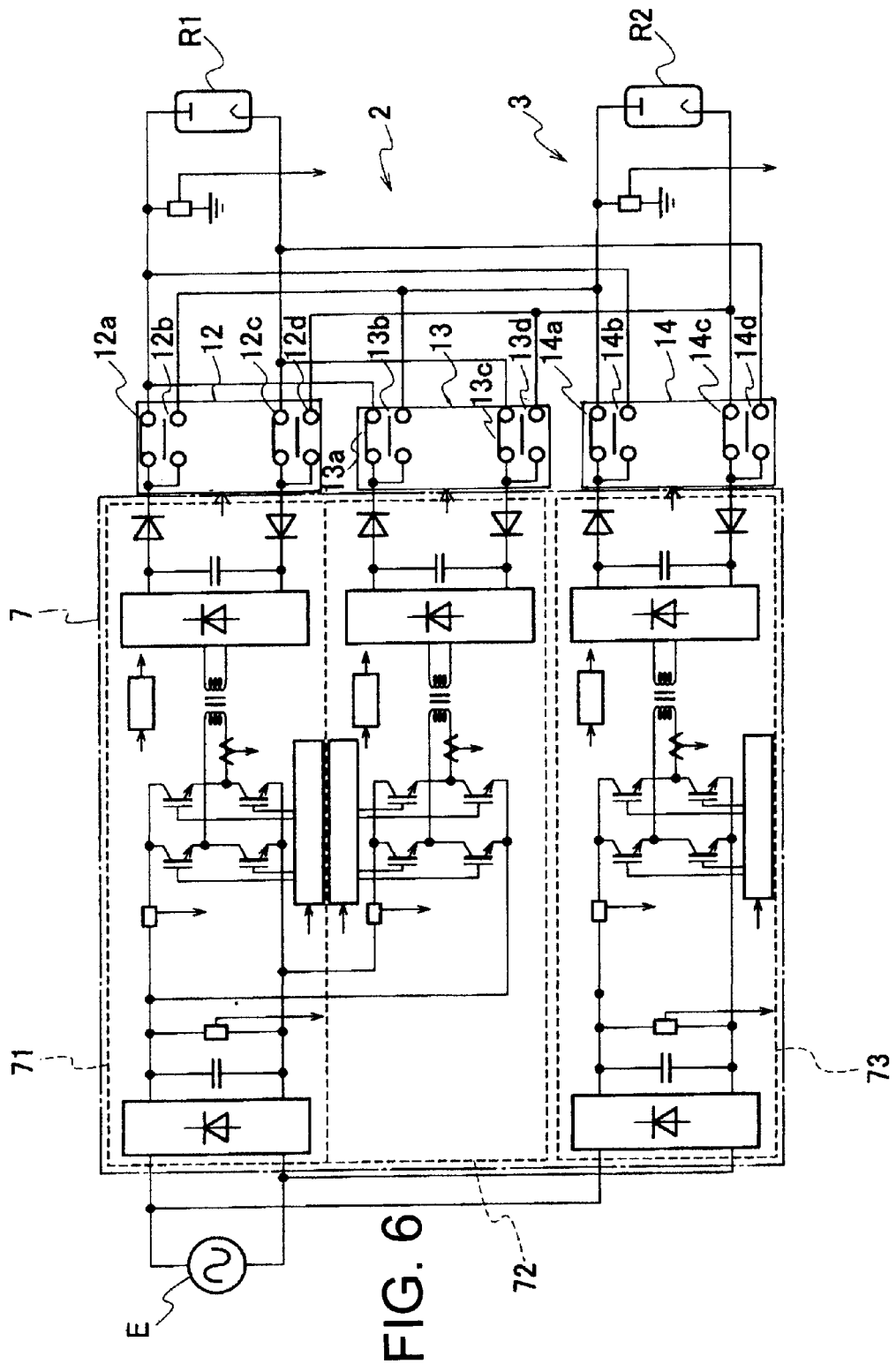
FIG. 6 is a circuit schematic showing a circuit configuration of the high voltage generator according to the second embodiment of the present invention.

FIG. 6 is a circuit schematic showing a circuit configuration of the high voltage generator according to the second embodiment of the present invention. As mentioned above, two high voltage generators are connected with one imaging system, e. g, the first imaging system 2. The two high voltage generators are represented as a first high voltage generator 71 and a second high voltage generator 72 in the second embodiment.

The other imaging system, i. e, the second imaging system 3 in this case, is connected with a single high voltage generator, which is represented as a third high voltage generator 73 in the second embodiment. Of course, an embodiment in which a single high voltage generator is connected with the first imaging system 2 while two high voltage generators are connected with the second imaging system 3 may be made.

The first to third high voltage generators 71 to 73 have a same circuit configuration as shown in FIG. 6. However, the first to third high voltage generators 71 to 73 are connected with X-ray tubes R as follows.

The first high voltage generator 71, supplying a high voltage to the first imaging system 2, is connected with a first X-ray tube R1 through switches 12a and 12c of a switching device 12 as shown in FIG. 6. On the other hand, the second high voltage generator 72 is connected with the first X-ray tube R1 through switches 13a and 13c of a switching device 13.

That is, the first high voltage generator 71 and the second high voltage generator 72 are connected with the first X-ray tube R1. In this case, an output toward the first X-ray tube R1 is one which a just single high voltage generator cannot supply sufficiently. Therefore, exposing a radiation having a desired power toward an object P from the first X-ray tube R1 needs applying high voltages to the first X-ray tube R1 by cooperation working of the first high voltage generator 71 and the second high voltage generator 72. For that matter, the second high voltage generator 72, connected with the first high voltage generator 71 in parallel, is an essential element.

Alternatively, the second high voltage generator 72 becomes a standby device in case where an abnormality occurs in the first high voltage generator 71 when the first high voltage generator 71 can output the power required for the X-ray diagnostic apparatus for oneself. Therefore, both the switches 13*a* and 13*c* shown in FIG. 6 are opened while the first high voltage generator 71 works normally.

The third high voltage generator 73 is connected with a second X-ray tube R2 through switches 14*a* and 14*c* of a switching device 14. The third high voltage generator 73 can output a necessary power to the second X-ray tube R2. Further, a switch 14*b* is connected between the switch 12*a* and the first X-ray tube R1 while a switch 14*d* is connected between the switch 12*c* and the first X-ray tube R1. On the other hand, switches 12*b* and 13*b* are connected between the switch 14*a* and a second X-ray tube R2 while switches 12*d* and 13*d* are connected between the switch 14*c* and the second X-ray tube R2.

Connection among the first, second and third high voltage generators 71, 72 and 73 as described above makes it possible to apply high voltages to the first X-ray tube R1 and the second X-ray tube R2 from at least one of high voltage generators working normally even though an abnormality occurs in one of the high voltage generators 71, 72 and 73.

Figure 7:
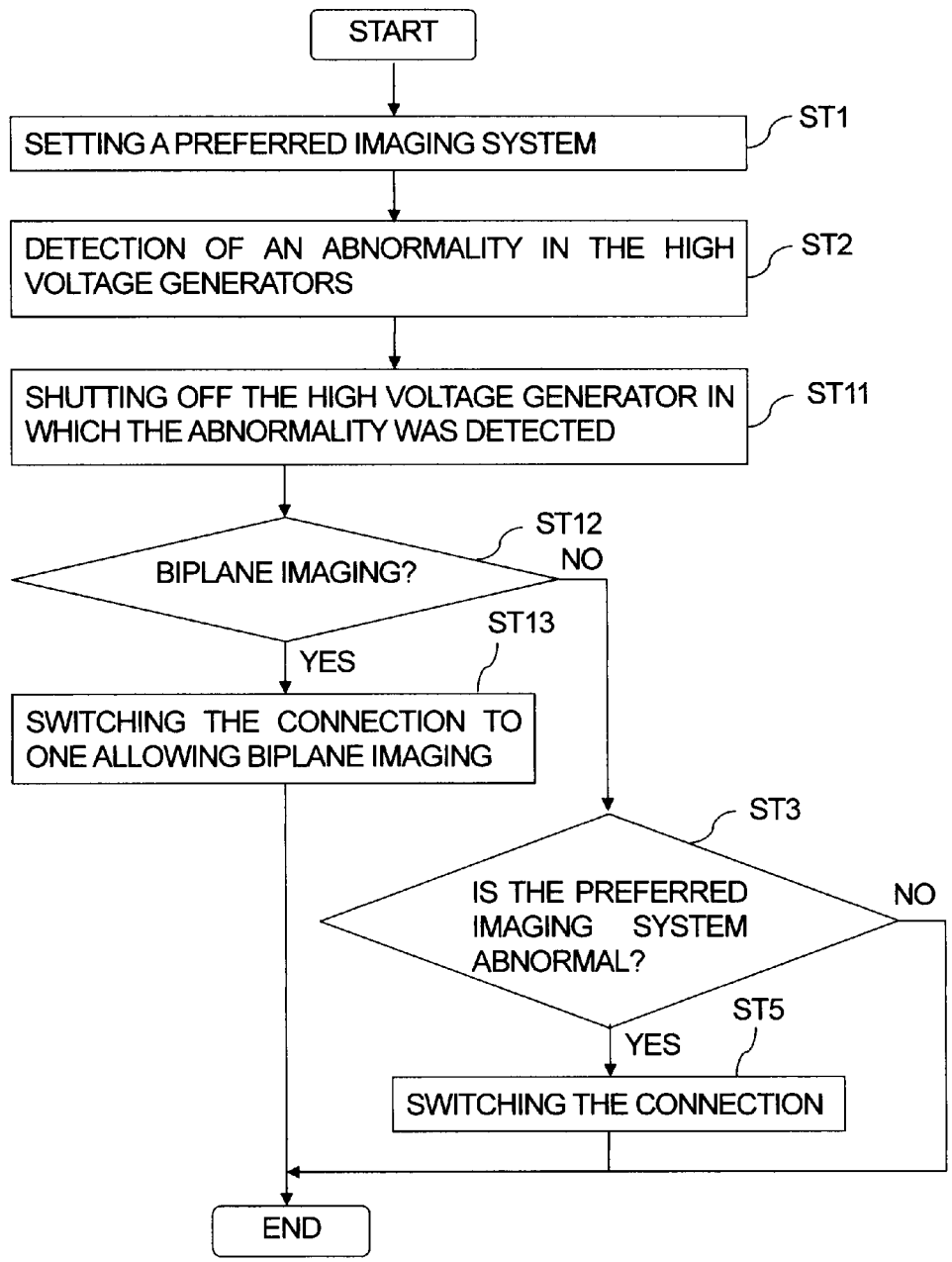
FIG. 7 is a flowchart showing a flow of a rough control in case where an abnormality occurred in the X-ray diagnostic apparatus according to the second embodiment of the present invention.

Next, a control of the X-ray diagnostic apparatus 1 when an abnormality detection unit detects an abnormality in the high voltage generating unit 7 will be described. FIG. 7 is a flowchart showing a flow of a rough control in case where an abnormality occurred in the X-ray diagnostic apparatus according to the second embodiment of the present invention. Setting a preferentially used imaging system (ST1), an abnormality detection in the high voltage generating unit 7 and recognition of the abnormality by the control unit 11 (ST2) are as explained in the first embodiment.

If the control unit 11 recognizes an abnormality in one of the high voltage generators (ST2), the control unit 11 opens the switches corresponding to the high voltage generator, in which abnormality occurred, to shut off the high voltage generator from the X-ray tube R (ST11).

Subsequently, the control unit 11 recognizes whether the X-ray diagnostic apparatus 1 is to be used as a biplane type of apparatus or not (ST12). Whether the X-ray diagnostic apparatus 1 is used as a biplane type or a single plane type in case where an abnormality has occurred in one of the high voltage generators may be preset. Alternatively, the X-ray diagnostic apparatus 1 may be configure to allow setting whether the apparatus 1 is used as a biplane type or a single plane type after an abnormality occurred in one of the high voltage generators.

When the X-ray diagnostic apparatus 1 is used as a biplane type (YES in ST12), the control unit 11 controls the switching device 13 to switch the connections of normally working high voltage generators into the combination by which the X-ray diagnostic apparatus 1 can be used as a biplane type (ST13).

Specifically, Wan abnormality is detected in the first high voltage generator 71 for which the second high voltage generator 72 is a standby, the switches 13*a* and 13*c* are closed while the switches 12*a* and 12*c* are opened, in order to apply a high voltage from the second high voltage generator 72 to the first X-ray tube R1. Herewith, a high voltage is applied from the second high voltage generator 72 to the first X-ray tube R1. To the contrary, if an abnormality is detected in the second high voltage generator 72, the first high voltage generator 71 is continued to be connected with the first X-ray tube R1 as it is without switching because the second high voltage generator 72 is a standby for the first high voltage generator 71.

Incidentally, the third high voltage generator 73 also can apply a high voltage to the first X-ray tube R1 as mentioned above. However, the third high voltage generator 73 have to apply a high voltage to the second X-ray tube R2 through the switches 14*a* and 14*c* to use the X-ray diagnostic apparatus 1 as a biplane type. Therefore, if an abnormality has occurred in the first high voltage generator 71 while both the second high voltage generator 72 and the third high voltage generator 73 work normally, the second high voltage generator 72 applies a high voltage to the first X-ray tube R1 while the third high voltage generator 73 applies a high voltage to the second X-ray tube R2 as mentioned above. Alternatively, if an abnormality has occurred in the second high voltage generator 72, the first high voltage generator 71 applies a high voltage to the first X-ray tube R1 while the third high voltage generator 73 applies a high voltage to the second X-ray tube R2.

As described above, when the second high voltage generator 72 is a standby, the above mentioned switching makes it possible to use the X-ray diagnostic apparatus 1 as a biplane type regardless of which imaging system is the preferentially used imaging system.

On the other hand, when the second high voltage generator 72 is an essential element to work with the first high voltage generator 71 and an abnormality occurs in one of the second high voltage generator 72 and the first high voltage generator 71, the X-ray diagnostic apparatus 1 can still be used as a biplane type. However, a power of high voltage which can be applied to the first X-ray tube R1 becomes insufficient, which makes a use of the first X-ray tube R1 limited. Accordingly, explanation will be made for each case with regard to which imaging system is the preferentially used imaging system.

When the first imaging system 2 is the preferentially used imaging system and an abnormality has occurred in the first high voltage generator 71, a power from only the second high voltage generator 72 is insufficient. Accordingly, the control unit 11 switches the switching device 14 to connect the third high voltage generator 73 with the first X-ray tube R1. That is, since the third high voltage generator 73 can apply a sufficient high voltage to an X-ray tube R for oneself, the third high voltage generator 73 is connected with the first X-ray tube R1 of the preferentially used first imaging system 2. On the other hand, the normally working the second high voltage generator 72 is connected with the second X-ray tube R2, which had been connected with the third high voltage generator 73 to use the X-ray diagnostic apparatus 1 as a biplane type. Such switching makes it possible to use the first imaging system 2 preferentially as well as use the X-ray diagnostic apparatus 1 as a biplane type.

If an abnormality has occurred in the second high voltage generator 72, the third high voltage generator 73 is connected with the first X-ray tube R1 of the preferentially used first imaging system 2 while the normally working first high voltage generator 71 is connected with the second X-ray tube R2, which had been connected with the third high voltage generator 73, in order to use the X-ray diagnostic apparatus 1 as a biplane type. Such switching makes it possible to use the first imaging system 2 preferentially as well as use the X-ray diagnostic apparatus 1 as a biplane type.

Alternatively, when the first imaging system 2 is preferentially used and an abnormality has occurred in the third high voltage generator 73, switching is performed as follows. In this case, the third high voltage generator 73 is shut off from the second X-ray tube R2 as mentioned above. However, the X-ray diagnostic apparatus 1 works as a single plane type if nothing is done. Here, the X-ray diagnostic apparatus 1 is to be used as a biplane type. For that purpose, one of the first high voltage generator 71 and the second high voltage generator 72 is connected with the second X-ray tube R2. Herewith, the X-ray diagnostic apparatus 1 can be used as a biplane type at least.

Figure 8:
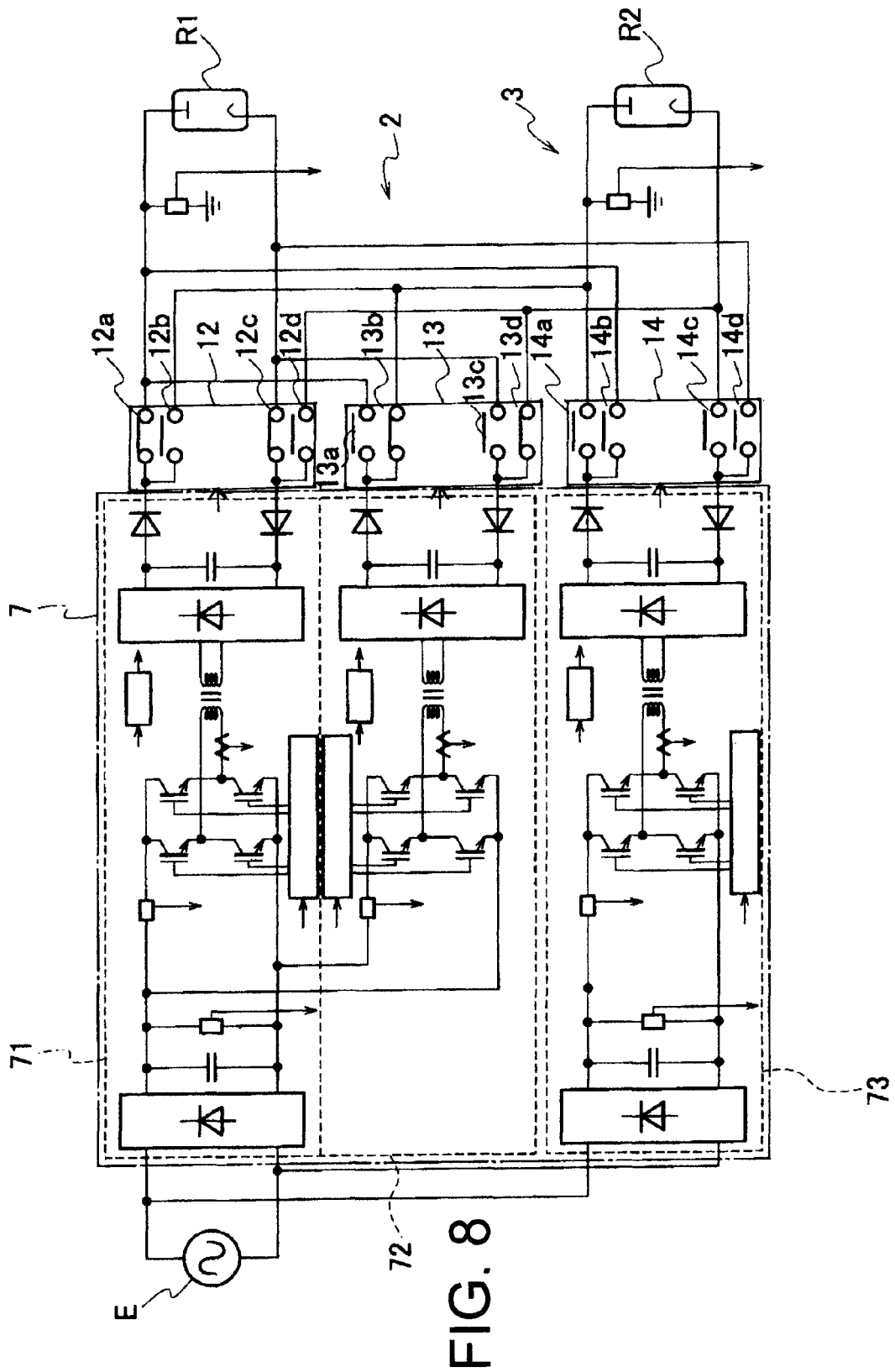
FIG. 8 is a circuit schematic showing a configuration of the circuit shown in FIG. 6 in case where an abnormality occurred in a part of the circuit.

FIG. 8 is a circuit schematic showing a configuration of the circuit shown in FIG. 6 in case where an abnormality occurred in a part of the circuit. As shown in FIG. 8, the switches 13a and 13c are opened while the switches 13b and 13d are closed for example. Herewith, the second X-ray tube R2 is connected with the switches 13b and 13d. Therefore, the normally working second high voltage generator 72 can apply a high voltage to the second X-ray tube R2 of the second imaging system 3.

Next, a case where the second imaging system 3 is preferentially used will be described. If an abnormality has occurred in one of the first high voltage generator 71 and the second high voltage generator 72, a sufficient high voltage is not applied to the first X-ray tube R1 of the first imaging system 2. However, the third high voltage generator 73 is working normally. Therefore, a sufficient high voltage is applied to the second X-ray tube R2 of the preferentially used second imaging system 3. Accordingly, one of the first high voltage generator 71 and the second high voltage generator 72 is connected with the first X-ray tube R1 while the third high voltage generator 73 is connected with the second X-ray tube R2. Consequently, the second imaging system 3 can be preferentially used with keeping use of the X-ray diagnostic apparatus 1 as a biplane type.

On the other hand, if an abnormality has occurred in the third high voltage generator 73, the normally working first high voltage generator 71 and the normally working second high voltage generator 72 are severally connected to the first X-ray tube R1 and the second X-ray tube R2 to use the X-ray diagnostic apparatus 1 as a biplane type. By the connection in this way, the X-ray diagnostic apparatus 1 can be used as a biplane type at least. For example, the switching devices 13 and 14 are controlled so that a high voltage from the normally working second high voltage generator 72 is applied to the second X-ray tube R2 as shown in FIG. 8.

When the X-ray diagnostic apparatus 1 is not used as a biplane type but a single plane type (NO in ST12), whether the high voltage generator of which abnormality has been detected is to power the preferentially used imaging system or not is determined (ST3), and the X-ray diagnostic apparatus 1 is controlled as follows.

First, a case where the second high voltage generator 72 is a standby and the first imaging system 2 is preferentially used as a single plane type will be described. If an abnormality occurs in the first high voltage generator 71 (YES in T3), the control unit 11 switches the switching device 13 to connect the second high voltage generator 72 with the first X-ray tube R1 (ST5). This connection makes it possible to use the first imaging system 2 preferentially. Alternatively, if an abnormality occurs in the second high voltage generator 72, the first high voltage generator 71 is continued to be connected with the first X-ray tube R1 as it is (ST5). Herewith, the first imaging system 2 can be used preferentially.

Note that, it is being assumed that the first imaging system 2 is used preferentially. Therefore, an abnormality in the third high voltage generator 73 does not affect the preferential use of the first imaging system 2 (NO in ST3).

Next, a case where the second high voltage generator 72 is a standby and the second imaging system 3 is preferentially used as a single plane type will be described. In this case, an abnormality in the first high voltage generator 71 or the second high voltage generator 72 does not affect the preferential use of the second imaging system 3 (NO in SD), so long as the third high voltage generator 73, which applies a high voltage to the second X-ray tube R2 of the second imaging system 3, works normally.

Alternatively, if an abnormality occurs in the third high voltage generator 73 (YES in SD), one of the first high voltage generator 71 and the second high voltage generator 72 is connected with the second X-ray tube R2 to keep the preferential use of the second imaging system 3 (ST5).

Next, a case where the second high voltage generator 72 is an essential element which works together with the first high voltage generator 71 and the first imaging system 2 is used preferentially as a single plane type will be described. In this case, only one of the first high voltage generator 71 and the second high voltage generator 72 cannot apply a sufficient high voltage to an X-ray tube R as described above. Therefore, if the first imaging system 2 is used preferentially and an abnormality has occurred in one of the first high voltage generator 71 and the second high voltage generator 72 (YES in SD), both the first high voltage generator 71 and the second high voltage generator 72 are shut off from the first X-ray tube R1 while the third high voltage generator 73 is connected with the first X-ray tube R1 (ST5). By this connection, the first imaging system 2 can be used preferentially as a single plane type though a high voltage is not applied to the second X-ray tube R2.

Alternatively, even if an abnormality has occurred in the third high voltage generator 73, the preferential use of the first imaging system 2 is not affected (NO in SD) since the third high voltage generator 73 does not apply a high voltage to the preferentially used first imaging system 2, i.e., the third high voltage generator 73 applies a high voltage to the second imaging system 3 which is not used preferentially.

Next, a case where the second high voltage generator 72 is an essential element which works together with the first high voltage generator 71 and the second imaging system 3 is used preferentially as a single plane type will be described. In this case, even though an abnormality has occurred in one of the first high voltage generator 71 and the second high voltage generator 72, the preferential use of the second imaging system 3 is not affected (NO in SD) since any of the first high voltage generator 71 and the second high voltage generator 72 does not apply a high voltage to the preferentially used second imaging system 3.

Alternatively, if an abnormality has occurred in the third high voltage generator 73 which applies a high voltage to the second X-ray tube R2 of the second imaging system 3 (YES in ST3), both the first high voltage generator 71 and the second high voltage generator 72 each working normally are connected with the second X-ray tube R2 (ST5). By this connection, a sufficient high voltage can be applied to the second X-ray tube R2 of the preferentially used second imaging system 3.

That is, the switching devices 12, 13 and 14 can be controlled to switch from an output from a high voltage generator of which abnormality has been detected toward the corresponding X-ray generator to an output from at least one of high voltage generators powering a common X-ray generator toward the corresponding X-ray generator. Under such a control, a high voltage is applied to the preferentially used imaging system steadily. Therefore, even though an abnormality occurs in a high voltage generator corresponding to one plane necessary for diagnosis, the one plane can be used continuously by an output from a high voltage generator corresponding to the other plane with adopting an inexpensive configuration. Consequently, a restriction in use of an apparatus due to an abnormality can be narrowed to increase safety of an object and a biplane type of X-ray diagnostic apparatus which keeps convenience to an operator can be obtained.

(Third Embodiment)

Next, the third embodiment of the present invention will be described. Note that, the explanation for the same elements of the third embodiment as those explained in the above-mentioned first or second embodiment is omitted for avoiding duplication.

Figure 9:
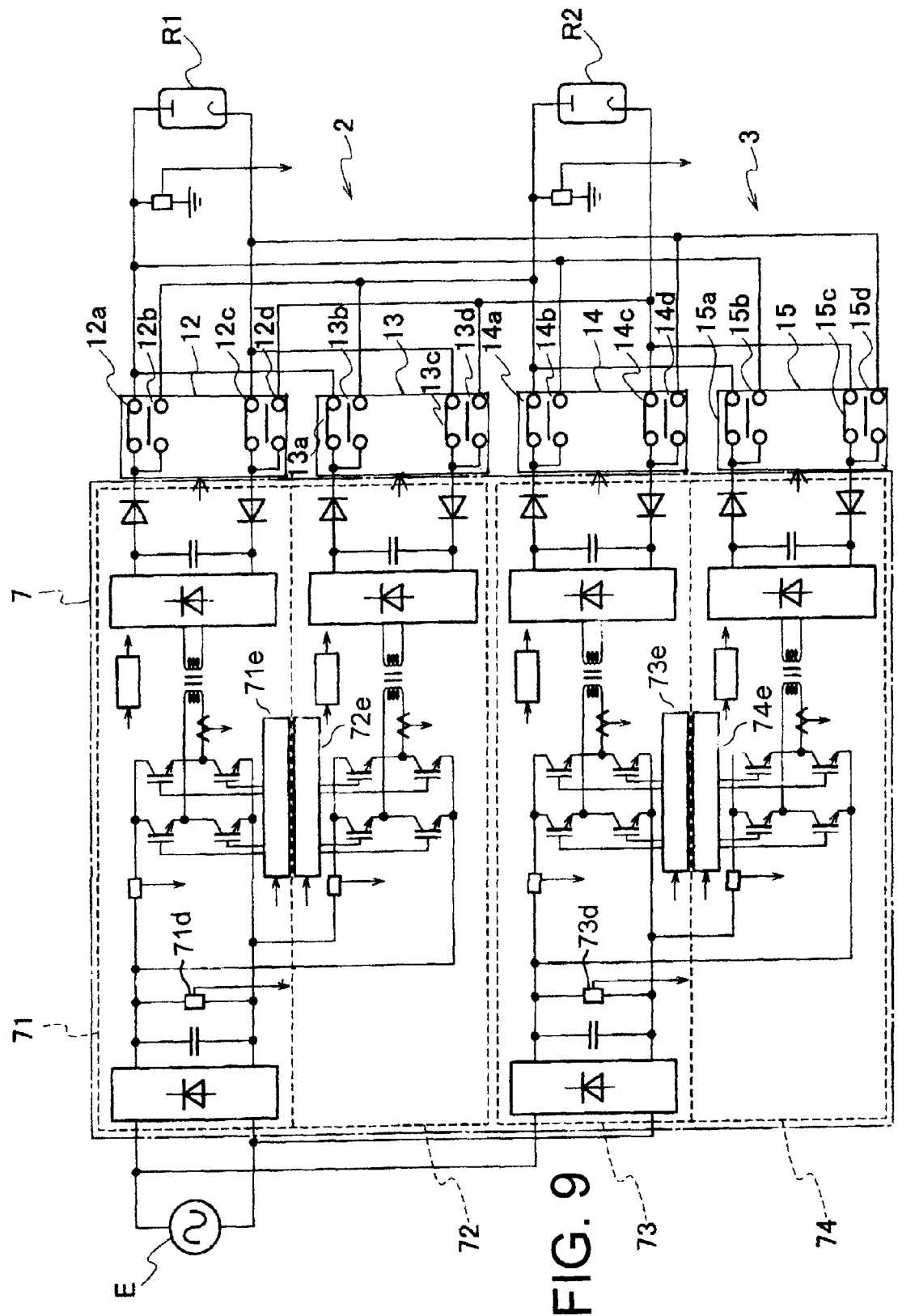
FIG. 9 is a circuit schematic showing a circuit configuration of the high voltage generator according to the third embodiment of the present invention.

The third embodiment is different from the first or second embodiment in the point that plural (two) high voltage generators are provided to apply high voltages each of plural imaging systems. As shown in FIG. 9, in the third embodiment, a first high voltage generator 71 and a second high voltage generator 72 are connected with a first X-ray tube R1 for applying high voltages while a third high voltage generator 73 and a fourth high voltage generator 74 are connected with a second X-ray tube R2 for applying high voltages. The first high voltage generator 71 is connected with the second high voltage generator 72 in parallel while the third high voltage generator 73 is connected with the fourth high voltage generator 74 in parallel.

Since the above mentioned configuration is adopted, not only a full wave rectifying circuit and a condenser for changing of an alternating current supplied from a commercial power E into a direct current by rectification and smoothing but also a voltage detection device 71d are shared by the first high voltage generator 71 and the second high voltage generator 72. Similarly, a full wave rectifying circuit, a condenser and a voltage detection device 73d are shared by the third high voltage generator 73 and the fourth high voltage generator 74. Each of the main circuit configurations in the first to fourth high voltage generator 71 to 74 is similarly to that explained in the above described first or second embodiment. Here, inverter drive circuits included in the first to fourth high voltage generator 71 to 74 are represented as 71e, 72e, 73e and 74e respectively. Further, the voltage detection device common to the first high voltage generator 71 and the second high voltage generator 72 is represented as 71 d while the voltage detection device common to the third high voltage generator 73 and the fourth high voltage generator 74 is represented as 73d.

Further, four switching devices 12, 13, 14 and 15 switch between the first to fourth high voltage generator 71 to 74 and the first and second X-ray tubes R1 and R2. Specifically, the respective switching devices 12, 13, 14 and 15 have four switches 12a, 12b, 12c, 12d, 13a, 13b, 13c, 13d, 14a, 14b, 14c, 14d, 15a, 15b, 15c and 15d. Closing the two switches 12a and 12c of the switching device 12 connects the first high voltage generator 71 with the first X-ray tube R1 while closing the two switches 12b and 12d connects the first high voltage generator 71 with the second X-ray tube R2. Same applies to the respective switching devices 13, 14 and 15.

FIG. 10 is a table showing an example of method for controlling the circuit shown in FIG. 9 in case where an abnormality occurred in a part of the circuit. In the third embodiment, it is assumed that any of the high voltage generators 71, 72, 73 and 74 cannot output a sufficient high voltage to be applied to an X-ray tube R for oneself.

However, a sufficient high voltage can be applied to an X-ray tube R by two high voltage generators. In the table of FIG. 10, a case where a sufficient high voltage can be applied to an X-ray tube R1 or R2 is indicated as "FULL" on the columns of respective X-ray tube outputs R1 OP and R2 OP in "OPERATION PANEL DISPLAY" while another case where a sufficient high voltage cannot be applied is indicated as "NOT FULL".

When a ratio in outputs from two high voltage generators toward a single X-ray tube R is 1:1, applying a high voltage to the X-ray tube R by one of the two high voltage generators allows the X-ray tube R to output 50% of the maximum power. Therefore, in this case, indications of "100%" and "50%"for the maximum outputs from the respective X-ray tubes R1 and R2 may be used instead of the indications of "FULL" and "NOT FULL" for the outputs from the respective X-ray tubes R1 and R2.

The table shows items on the top line. That is, items of "DETECTED ABNORMALITY", "INVERTER DRIVE CIRCUIT", "SWITCHING DEVICE" and "OPERATION PANEL DISPLAY" are shown from the most left column on the table. The operation panel means the input device 10 for example. The inverter drive circuit and the switching device are provided in each of the first to fourth high voltage generators, and therefore, they are indicated by "71e, 72e, 73e and 74e" and "12, 13, 14 and 15" in sequence respectively.

Just below the columns indicating the items, parameters in a case where the detected abnormality is none, i.e., nominal, are indicated for comparison. When no abnormality occurs in any of the high voltage generators 71, 72, 73 and 74, the respective inverter drive circuits 71e, 72e, 73e and 74e work normally. Therefore, a sufficient high voltage is applied to any of the first X-ray tube R1 and the second X-ray tube R2. Accordingly, "FULL" is displayed on each of the columns of "R1 OP" meaning the first X-ray tube output and "R2 OP" meaning the second X-ray tube output in "OPERATION PANEL DISPLAY". In this case, the X-ray diagnostic apparatus 1 can be used as a biplane type of apparatus as a matter of course.

In the column below "NORMAL", "POWER ABNORMALITY" is displayed as a detected abnormality. This abnormality is one detected by a voltage detection device 71d or 73d in the high voltage generators, and represents one that no power or an insufficient power is supplied to the inverter drive circuits 71e and 72e or the inverter drive circuits 73e and 74e and the like, The table shown in FIG. 10 presents a case of a power abnormality detected by the voltage detection device 71d. The voltage detection device 71d is an abnormality detection unit which detects whether an appropriate voltage is applied to each of the first high voltage generator 71 and the second high voltage generator 72 or not. Therefore, if the voltage detection device 71d detects an abnormality in power supply, both the inverter drive circuit 71e in the first high voltage generator 71 and the inverter drive circuit 72e in the second high voltage generator 72 stop. On the other hand, the voltage detection device 73d, for detecting an abnormality in power supplies toward the third high voltage generator 73 and the fourth high voltage generator 74, detects no abnormality. Therefore, the inverter drive circuit 73e in the third high voltage generator 73 and the inverter drive circuit 74e in the fourth high voltage generator 74 are driven normally, which are indicated as "OPR" on the table of FIG. 10.

If the inverter drive circuit 71e and the inverter drive circuit 72e stop, a high voltage is not applied to the first X-ray tube R1. In this case, the control unit 11 has three selectable choices with regard to control as shown in FIG. 10.

The first choice is using the X-ray diagnostic apparatus 1 as a biplane type. A control of the switching devices corresponding to this choice is displayed in the upper columns of the "POWER ABNORMALITY" section in FIG. 10.

In case of POWER ABNORMALITY", both the inverter drive circuits 71e and 72e stop as mentioned above. Therefore, all switches in the switching devices 12 and 13 are opened to shut off both the first high voltage generator 71 and the second high voltage generator 72 from any of the first X-ray tube R1 and the second X-ray tube R2. This state is indicated with "OFF"s in the table of FIG. 10.

When the X-ray diagnostic apparatus 1 is used as a biplane type, it is necessary to apply a high voltage to the first X-ray tube R1. For that purpose, the switches 14a and 14c are opened while the switches 14b and 14d are closed. The switches 14b and 14d are connected with the first X-ray tube R1. Therefore, closing the switches 14b and 14d allows the third high voltage generator 73 to apply a high voltage to the first X-ray tube R1.

Moreover, the switches 15a and 15c are closed. Therefore, a high voltage from the fourth high voltage generator 74 is applied to the second X-ray tube R2. By this switching, a high voltage is applied to any of the first X-ray tube R1 and the second X-ray tube R2. Consequently, the X-ray diagnostic apparatus 1 can be used as a biplane type.

However, none of the first to fourth high voltage generators 71 to 74 is able to apply a sufficiently high voltage to an X-ray tube R only by itself as mentioned above. Therefore, a sufficiently high voltage cannot be applied to the first X-ray tube R1 even though an output from the third high voltage generator 73, which had applied a high voltage to the second X-ray tube R2, is directed to the first X-ray tube R1 due to halts of the first high voltage generator 71 and the second high voltage generator 72.

On the other hand, the high voltage, which had been applied to the second X-ray tube R2, is also directed to the first X-ray tube R1. Therefore, a sufficiently high voltage is not applied to the second X-ray tube R2. A state in which a sufficiently high voltage is not applied to the first X-ray tube R1 or the second X-ray tube R2 is indicated as "NOT FULL" in the table of FIG. 10.

The other two choices selectable by the control unit 11 as a control way are a case where high voltages are directed to one X-ray tube R and a case where high voltages are directed to the other one R, to use the X-ray diagnostic apparatus 1 not as a biplane type but as a single plane type. In using the X-ray diagnostic apparatus 1 as a single plane type, one choice is to concentrate the high voltages on the first X-ray tube R1 and another choice is to concentrate the high voltages on the second X-ray tube R2. Selecting between those choices is made depending on which imaging system is used preferentially for example.

When the high voltages are concentrated on the first X-ray tube R1 to use the first imaging system 2, the control unit 11 closes the switches 14b and 14d, opens the switches 14a and 14c, closes the switches 15b and 15d, and opens the switches 15a and 15c. By this switching, all the high voltages outputted from the third and fourth high voltage generators 73 and 74 are applied to the first X-ray tube R1. Therefore, in the table of FIG. 10, the column in the section "R1 OP" is indicated as "FULL" while the column in the section "R2 OP" is indicated as "0". In addition, the X-ray diagnostic apparatus 1 cannot be used as a biplane type in this case as described above. Therefore, the column in the section "BIPLANE" is indicated as "IMPOSSIBLE".

That is, W an abnormality in power supply toward the high voltage generators 71 and 72 powering the first X-ray tube R1 has been detected by an abnormality detection unit, the switching devices 12, 13, 14 and 15 can be controlled to switch from outputs from the high voltage generators 71 and 72, in which abnormality has been detected, toward the first X-ray tube R1 to an output from at least one of the high voltage generators 73 and 74, which had powered the second X-ray tube R2, toward the first X-ray tube R1.

On the other hand, when the high voltages are concentrated on the second X-ray tube R2 to use the second imaging system 3, the control unit 11 closes the switches 14a and 14c, opens the switches 14b and 14d, closes the switches 15a and 15c, and opens the switches 15b and 15d. By this switching, all the high voltages outputted from the third and fourth high voltage generators 73 and 74 are applied to the second X-ray tube R2. Therefore, in the table of FIG. 10, the column in the section "R1 OP" is indicated as "0" while the column in the section "R2 OP" is indicated as "FULL". In addition, the X-ray diagnostic apparatus 1 cannot be used as a biplane type in this case as described above. Therefore, the column in the section "BIPLANE" is indicated as "IMPOSSIBLE".

In case of "POWER ABNORMALITY", two high voltage generators which are mutually connected in parallel, i.e., both the first and second high voltage generators 71 and 72, or both the third and fourth high voltage generators 73 and 74, stop as mentioned above.

On the other hand, an abnormality occurrence shown by one abnormality detection unit of the fuse shutoff detection devices, current detection devices and temperature detection devices means an abnormality occurrence in an inverter circuit. Therefore, only the high voltage generator in which the abnormality occurred stops. The table of FIG. 10 shows an example case where an abnormality occurred in the inverter circuit 72c of the second high voltage generator 72. Hereinafter, explanation will be made for this example case.

In this case, the inverter drive circuit 72e halts. However, the remaining the inverter drive circuits 71e, 73e and 74e operate and the first, third and fourth high voltage generators 71, 73 and 74 work.

That is the three out of the four high voltage generators work normally. Therefore, the control unit 11 controls a way to apply the high voltages from the three high voltage generators to the two X-ray tubes R. In this case, no choice is made to use the X-ray diagnostic apparatus 1 as a single plane type and the X-ray diagnostic apparatus 1 is used as a biplane type in any case.

Specifically, in the example case shown in FIG. 10, it is necessary to determine whether the high voltage from the third high voltage generator 73 is directed to the first X-ray tube R1 or the second X-ray tube R2.

When the high voltage from the third high voltage generator 73 is directed to the first X-ray tube R1, a control is made so that the switches 14b and 14d are closed and the switches 14a and 14c are opened. Under the above described control of the switching device 14, the high voltages from the first and third high voltage generators 71 and 73 are applied to the first X-ray tube R1.

On the other hand, the third high voltage generator 73, which had applied the high voltage to the second X-ray tube R2 originally, begins to apply the high voltage to the first X-ray tube R1. Therefore, the high voltage applied to the second X-ray tube R2 becomes insufficient. That is, the output of the first X-ray tube R1 becomes "FULL" while the output of the second X-ray tube R2 becomes "NOT FULL". However, the X-ray diagnostic apparatus 1 can be used as a biplane type even though the insufficient high voltage is applied to the second X-ray tube R2.

Alternatively, when the high voltage from the third high voltage generator 73 is directed to the second X-ray tube R2, a control is made so that the switches 14a and 14c are closed and the switches 14b and 14d are opened. That is, the control unit 11 controls not to change a previous operation state. Under the above described control of the switching device 14, the high voltages from the third and fourth high voltage generators 73 and 74 are applied to the second X-ray tube R2.

On the other hand, it becomes only the first high voltage generator 71 that applies the high voltage to the first X-ray tube R1 due to the halt of the second high voltage generator 72. Therefore, the high voltage applied to the first X-ray tube R1 becomes insufficient. That is, the output of the first X-ray tube R1 becomes "NOT FULL". However, the sufficient high voltage continuously applied to the second X-ray tube R2 makes it possible to use the X-ray diagnostic apparatus 1 as a biplane type even though the insufficient high voltage is applied to the first X-ray tube R1.

Under such a control, a high voltage is applied to the preferentially used imaging system steadily. Therefore, even though an abnormality occurs in a high voltage generator corresponding to one plane necessary for diagnosis, the one plane can be used continuously by an output from a high voltage generator corresponding to the other plane with adopting an inexpensive configuration. Consequently, a restriction in use of an apparatus due to an abnormality can be narrowed to increase safety of an object and a biplane type of X-ray diagnostic apparatus which keeps convenience to an operator can be obtained.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the control unit is configured to set a preferentially used imaging system in the above mentioned embodiments of the present invention. However, a preferential use setting unit configured to set a preferentially used imaging system may be provided as a dedicated unit. In this case, the control unit is configured to specify the preferentially used imaging system based on a setting result by the preferential use setting unit.

What is claimed is:

1. An X-ray diagnostic apparatus comprising:
   X-ray generators including a first X-ray generator and a second X-ray generator;
   X-ray detectors corresponding to said X-ray generators;
   high voltage generators configured to apply voltages to said X-ray generators;
   a switching device configured to switch outputs from said high voltage generators to said X-ray generators, the high voltage generators including a first high voltage generator and a second high voltage generator;
   an abnormality detection unit configured to detect an abnormality in said high voltage generators; and
   a control unit configured to control said switching device to switch from an output from the first high voltage generator, of which an abnormality has been detected by said abnormality detection unit, toward the first X-ray generator, to an output from the second high voltage generator toward the first X-ray generator,
   wherein said control unit is further configured to control said switching device to switch from an output from the first high voltage generator toward the first X-ray generator to an output from at least the second high voltage generator powering the second X-ray generator toward the first X-ray generator when an abnormality in power toward the first high voltage generator powering the first X-ray generator is detected by said abnormality detection unit, the second X-ray generator being different from the first X-ray generator.

2. An X-ray diagnostic apparatus of claim 1,
   wherein said high voltage generators further include a third high voltage generator powering the second X-ray generator and
   said control unit is further configured to control said switching device to switch from the output from the first high voltage generator, of which the abnormality has been detected, toward the first X-ray generator, to an output from the second high voltage generator powering the second X-ray generator toward the first X-ray generator.

3. An X-ray diagnostic apparatus of claim 1,
   wherein said abnormality detection unit includes at least one of a current detection device configured to detect a current in an inverter included in each of said high voltage generators, a voltage detection device configured to detect an input voltage into the inverter, a temperature detection device configured to detect a temperature of the inverter and a fuse shutoff detection device configured to detect a shutoff of a fuse in the inverter.

4. An X-ray diagnostic apparatus of claim 1, further comprising:
   a preferentially used imaging system of which the first X-ray generator is constantly powered by at least one of the high voltage generators without an abnormality,
   wherein said control unit is further configured to allow to set the preferentially used imaging system.

5. An X-ray diagnostic apparatus of claim 1, further comprising:
   a preferentially used imaging system of which the first X-ray generator is constantly powered by at least one of the high voltage generators without an abnormality,
   a preferential use setting unit configured to set the preferentially used imaging system,
   wherein said control unit is further configured to control said switching device to switch from the first high voltage generator, of which an abnormality has been detected, to the second high voltage generator based on a setting by said preferential use setting unit.

6. An X-ray diagnostic method comprising:
   detecting an abnormality in high voltage generators for applying voltages to X-ray generators;
   switching an output from a first high voltage generator of the high voltage generators, of which an abnormality has been detected, toward a corresponding first X-ray generator, to an output from another second high voltage generator of the high voltage generators toward the first X-ray generator;
   detecting projection data of an object by exposing an X-ray to the object using at least the first X-ray generator; and
   generating image data based on the detected projection data,
   wherein outputs from the first high voltage generator toward the first X-ray generator are switched to an output from at least the second high voltage generator powering a second X-ray generator toward the first X-ray generator when an abnormality in power toward the first high voltage generator powering the first X-ray generator is detected, the second X-ray generator being different from the first X-ray generator.

* * * * *